United States Patent [19]

Sampson et al.

[11] Patent Number: 4,504,465
[45] Date of Patent: Mar. 12, 1985

[54] COSMETIC STICKS

[75] Inventors: Ronald L. Sampson; David L. Shelton, both of Cincinnati, Ohio

[73] Assignee: The Proctor & Gamble Company, Cincinnati, Ohio

[21] Appl. No.: 164,613

[22] Filed: Jun. 30, 1980

Related U.S. Application Data

[63] Continuation-in-part of Ser. No. 123,238, Feb. 21, 1980, abandoned, which is a continuation-in-part of Ser. No. 66,710, Aug. 15, 1979, abandoned.

[51] Int. Cl.³ .................. A61K 7/32; A61K 7/34; A61K 7/36; A61K 7/38
[52] U.S. Cl. ................ 424/65; 424/DIG. 5; 424/66; 424/67; 424/68; 514/781
[58] Field of Search ............... 424/65, 66, 68, DIG. 5

[56] References Cited

U.S. PATENT DOCUMENTS

| | | | |
|---|---|---|---|
| 2,732,327 | 1/1956 | Teller | 424/DIG. 5 |
| 2,857,315 | 10/1958 | Teller | 424/DIG. 5 |
| 2,900,306 | 8/1959 | Slater | 424/DIG. 5 |
| 2,970,083 | 1/1961 | Bell | 424/68 |
| 3,259,545 | 7/1966 | Teller | 424/DIG. 5 |
| 3,325,367 | 6/1967 | Miechowski | 424/DIG. 5 |
| 3,472,940 | 10/1969 | Osipow et al. | 424/DIG. 5 |
| 3,553,316 | 1/1971 | Rubino | 424/DIG. 5 |
| 3,963,833 | 6/1976 | De Salva et al. | 424/DIG. 5 |
| 4,005,189 | 1/1977 | Reese et al. | 424/DIG. 5 |
| 4,049,792 | 9/1977 | Elsnau | 424/DIG. 5 |
| 4,120,948 | 10/1978 | Shelton | 424/DIG. 5 |
| 4,137,306 | 1/1979 | Rubino et al. | 424/DIG. 5 |
| 4,268,498 | 5/1981 | Gedeon et al. | 424/59 |

FOREIGN PATENT DOCUMENTS

| | | | |
|---|---|---|---|
| 1246168 | 8/1967 | Fed. Rep. of Germany | 424/DIG. 5 |
| 1024337 | 1/1953 | France | 424/65 |
| 624409 | 9/1961 | Italy | 424/358 |
| 50-52007 | 5/1975 | Japan | 424/70 |

OTHER PUBLICATIONS

Croda Cosmetic and Pharmaceutical Formulary 77 (1976 Revised 1979).

*Primary Examiner*—Dale R. Ore
*Attorney, Agent, or Firm*—Richard C. Witte; John V. Gorman; Douglas C. Mohl

[57] ABSTRACT

Stable, single phase soap gel cosmetic stick compositions comprising a polyhydric aliphatic alcohol, an ethylene oxide and/or propylene oxide condensation product and soap. Such cosmetic sticks are easily processed as well as being stable.

10 Claims, No Drawings

COSMETIC STICKS

CROSS REFERENCE TO RELATED APPLICATION

This is a continuation-in-part of our copending application Serial No. 123,238 filed February 21, 1980 which is a continuation-in-part of application Serial No. 066,710 filed August 15, 1979, both now abandoned.

TECHNICAL FIELD

The present invention relates to cosmetic compositions in the form of solid sticks. The compositions herein comprise a polyhydric alcohol, an ethylene oxide and/or propylene oxide condensation product and soap.

BACKGROUND ART

Attempts have been made to realize cosmetic sticks which deliver active ingredients to the skin such as deodorant materials via a vehicle which glides easily over the skin surface and which imparts a cooling sensation to the skin both during and after application. Soap-/alcohol gels can provide such cosmetic benefits. Examples of soap gels are disclosed in U.S. Pat. No. 2,732,327 Jan. 24, 1956 to Teller; U.S. Pat. No. 2,857,315, Oct. 21, 1958 to Teller; U.S. Pat. No. 2,900,306, Aug. 18, 1959 to Slater; and U.S. Pat. No. 2,970,083, Jan. 31, 1961 to Bell.

While soap gels are old as evidenced by the above patents, such gels are not completely satisfactory. Generally, soap gels require considerable time to set up and often exhibit syneresis at elevated temperatures.

It is, therefore, an object of the present invention to provide cosmetic soap gel sticks which have reduced set-up times and syneresis while being aesthetically pleasing.

It is a further object of the present invention to provide cosmetic sticks which, when a perfume is present, have greater perfume scent on the skin than in the package.

It is a further object of the present invention to provide such cosmetic sticks which effectively deliver deodorant materials to the skin.

It has been surprisingly discovered that the above objectives can be realized by formulating a stick comprising the ingredients described below.

All percentages used herein are by weight of the total composition unless otherwise designated.

DISCLOSURE OF INVENTION

The present invention relates to cosmetic stick compositions comprising from about 6% to about 70% of a polyhydric aliphatic alcohol, from about 3% to about 10% of a soap and from about 20% to about 80% of an ethylene oxide and/or propylene oxide condensation product.

DETAILED DESCRIPTION OF THE INVENTION

The essential elements of the cosmetic gel sticks of the present invention as well as optional components, composition preparation, and composition use are discussed in detail below:

POLYHYDRIC ALIPHATIC ALCOHOL

An essential component of the present cosmetic gel stick compositions is a polyhydric aliphatic alcohol containing 2 or 3 carbon atoms and from 2 to 3 hydroxyl groups. The polyhydric aliphatic alcohol component of the stick comprises from about 6% to about 70%, preferably from about 15% to 70%, by weight of the composition.

Suitable polyhydric alcohols for use in the gel compositions herein include ethylene glycol, propylene glycol, trimethylene glycol, and glycerine. The most preferred polyol is propylene glycol.

SOAP

Another essential component of the compositions herein is a gel forming agent. The gel forming agents used herein can be the sodium and potassium salts (i.e. soaps) of fatty acids containing from about 14 to 18 carbon atoms.

Soaps generally comprise from about 3% to about 10% by weight, preferably from about 4% to about 8% by weight of the composition. If soap concentrations lower than those specified are employed, the gels formed tend to be dimensionally unstable and tend to deform at summertime temperatures. If concentrations of soap above those specified are utilized, the gels formed tend to be too hard and do not exhibit desirable glide and application characteristics.

The fatty acid portion of the soap gel forming agents should be essentially pure saturated or unsaturated higher fatty acids having a $C_{14}$ to $C_{18}$ backbone. Suitable mixtures of such acids can be employed provided that such mixtures are free from significant proportions of other fatty acids of higher or lower chain length which substantially adversely affect or neutralize the desired gel forming effects.

Examples of fatty acids useful in synthesizing the gel forming agents herein include myristic, palmitic, stearic, oleic, linoleic, linolenic, margaric and the mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed oil, rosin acids, and greases. Conventional fractionation and/or hydrolysis techniques can be employed if necessary to obtain the requisite types of fatty acids from such materials.

Preferred fatty acid soap type gel forming agents include sodium stearate, sodium palmitate, potassium stearate, potassium palmitate and sodium myristate. The most preferred gel forming agent is sodium stearate.

Ethylene Oxide and/or Propylene Oxide Condensation Product

Still another essential component of the present composition is an ethylene oxide and/or propylene oxide condensation product having the following formula:

$$R(OC_3H_6)_a(OC_2H_4)_bOH$$

wherein R is either hydrogen or a hydrocarbon chain having from about 2 to 20 carbon atoms, preferably from about 4 to 18, a and b are each from 0 to 35 and a+b is from 5 to 35.

Examples of such products are a condensate of about 14 moles of propylene oxide with about one mole of butyl alcohol sold by Union Carbide under the name Fluid AP 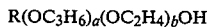; a polypropylene glycol having a molecular weight of 1200; a polyethylene glycol having a molecular weight of 420; a condensate of 20 moles of ethylene oxide and 5 moles of propylene oxide with one mole of cetyl alcohol; and a condensate of 15 moles of propylene oxide with one mole of stearyl alcohol. The preferred condensate is Fluid AP ®.

The condensate product is present in the compositions of the present invention at a level of from about 20% to about 80%, preferably from about 30% to about 70% by weight of the composition.

OPTIONAL COMPONENTS

The instant stick compositions can contain a variety of optional ingredients suitable for improving composition efficacy, stability, cosmetics and/or aesthetics. Such optional components include deodorant material, perfumes, dyes, pigments, coloring agents and the like.

A highly preferred optional component of the instant compositions is a material which helps retard alcohol evaporation and which acts as an antisyneresis agent. Especially preferred materials of this type are cellulose derivatives such as hydroxyalkylcelluloses. Especially preferred materials of this type are hydroxypropylcellulose compounds having the chemical formula:

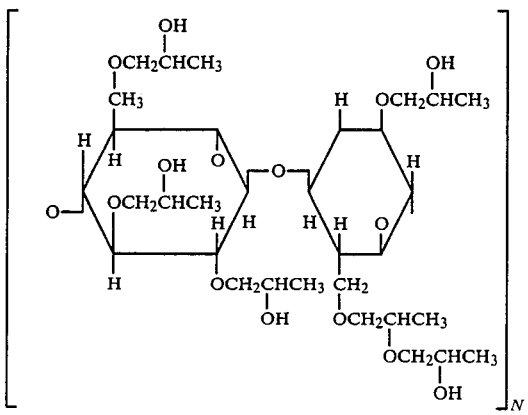

and wherein N is sufficiently large such that the total molecular weight of the material ranges from about 60,000 to 1,000,000. Such materials are sold under the tradename of Klucel ® by Hercules Incorporated. If present, such alcohol evaporation retarding agents and anti-syneresis agents comprise from about 0.1% to 5.0% by weight of the composition.

Another optional ingredient of the instant compositions is a conventional deodorant material. Suitable deodorants include bacteriostatic quaternary ammonium compounds such as cetyl-trimethylammonium bromide, cetyl pyridinium chloride, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmitoyl sarcosine, lauroyl sarcosine, N-myristoyl glycine, potassium N-lauroyl sarcosine and stearyl tri-methyl ammonium chloride. If present, deodorants generally comprise from about 0.1% to 1.0% by weight of the composition.

Another optional component is a short chain monohydric alcohol in an amount from about 0.1% to about 50.0%, preferably from about 1.0% to about 40.0%. Suitable alcohols include methanol, ethanol, N-propanol and isopropanol. The preferred alcohol is ethanol.

Other optional ingredients such as perfumes, dyes, pigments, coloring agents and the like, if present, comprise from about 0.1% to 1.5% by weight of the compositions.

METHOD OF MANUFACTURE

The gel sticks of the present invention are made by combining the ingredients in liquid form and pouring the mixture into a form having the desired shape. The present gel may be used as the gel portion of the antiperspirant sticks described and claimed in U.S. Pat. No. 4,202,879, May 13, 1980 to Shelton, incorporated herein by reference. A preferred antiperspirant stick is where the present gel forms a shell around the antiperspirant core.

COMPOSITION USE

The gel sticks herein are used by the consumer by rubbing the stick on the area of the body where application is desired. In the case of a deodorant stick the stick is rubbed in the axilla area to apply the deodorant agent.

EXAMPLES I–VIII

Given below are examples of compositions within the scope of the present invention. In addition, compositions containing similar materials as well as one which does not contain an appropriate condensation product are shown.

| Formulae: | I | II | III | IV | V | VI | VII | VIII |
|---|---|---|---|---|---|---|---|---|
| Ethanol | 20.0 | 7.5 | — | 20.0 | — | 20.0 | 20.0 | — |
| Propylene Glycol | 15.5 | 27.9 | 24.0 | 25.5 | 24.0 | 25.5 | 20.0 | 24.0 |
| Fluid AP ®[1] | 57.5 | 55.6 | — | — | — | — | — | 37.25 |
| Witconol APM ®[2] | — | — | 67.25 | 47.5 | — | — | — | — |
| Carbitol ®[3] | — | — | — | — | 67.25 | 47.5 | — | — |
| Sodium Stearate | 7.0 | 6.5 | 6.25 | 7.0 | 6.25 | 7.0 | 7.0 | 7.25 |
| Misc. | — | 2.5 | 2.5 | — | 2.5 | — | 3.0 | 3.5 |
| Set-up-time (Min.) | 2 | 9 | 35 | 45 | 38 | 17 | 30 | 3 |

[1] Condensation product of one mole of butyl alcohol with 14 moles of propylene oxide supplied by Union Carbide Corporation.
[2] Condensation product of one mole of myristyl alcohol with three moles of propylene oxide supplied by Witco Chemical Company.
[3] Condensation product of one mole of butyl alcohol with two moles of ethylene oxide supplied by Union Carbide Corporation.

The above-mentioned compositions were made and poured into packages. The pour temperature of the compositions was 190° F. in each case. After pouring, the units were allowed to set at room temperature until gel set up was observed.

GEL SET-UP TIME (DEFINITION):

The time necessary for the gel to set up to the point where there are no visible signs of exudation during trimming.

It is seen that the compositions containing Fluid AP ® have significantly shorter set-up times than do the other compositions. The shorter times result in easier gel processing.

What is claimed is:
1. A cosmetic gel stick composition comprising:
   A. from about 6% to about 70% of an aliphatic, polyhydric alcohol having from 2 to 3 carbon atoms and from 2 to 3 hydroxyl groups;
   B. from about 3% to about 10% of a soap; and
   C. from about 20% to about 80% of a condensation product having the formula

$R(OC_3H_6)_a(OC_2H_4)_bOH$ wherein R is selected from the group consisting of hydrogen and hydrocarbon chains having from about 2 to about 20 carbon atoms, a and b are each from about 0 to about 35 and a+b is from about 5 to about 35.

2. A stick composition according to claim 1 which in addition contains from about 0.1% to about 1.0% of a deodorant material.

3. A stick composition according to claim 2 wherein the level of polyhydric alcohol is from about 15% to about 70%, the level of soap is from about 4% to about 8% and the level of the condensation product is from about 30% to about 70%.

4. A stick composition according to claim 3 wherein the soap is selected from the group consisting of a sodium salt and a potassium salt of a fatty acid containing from about 14 to about 18 carbon atoms and R in the condensation product is hydrocarbon chain having from about 4 to about 18 carbon atoms.

5. A stick composition according to claim 4 which in addition contains a monohydric alcohol selected from the group consisting of methanol, ethanol, isopropanol and n-propanol.

6. A stick composition according to claim 4 wherein the polyhydric alcohol is selected from the group consisting of ethylene glycol, propylene glycol, trimethylene glycol and glycerine.

7. A stick composition according to claim 6 wherein the soap is selected from the group consisting of sodium stearate, sodium palmitate, sodium myristate, potassium stearate and potassium palmitate.

8. A stick composition according to claim 7 wherein the polyhydric alcohol is propylene glycol.

9. A stick composition according to claim 8 wherein the soap is sodium stearate.

10. A stick composition according to claim 9 wherein the condensation product is the reaction product of one mole of butyl alcohol with about 14 moles of propylene oxide.

* * * * *